US012559523B2

(12) United States Patent
Shailubhai et al.

(10) Patent No.: US 12,559,523 B2
(45) Date of Patent: Feb. 24, 2026

(54) COMPOSITIONS COMPRISING CHEMERIN ANALOGS AND METHODS OF USE

(71) Applicant: OKYO Pharma Limited, St. Peter Port (GG)

(72) Inventors: Kunwar Shailubhai, Line Lexington, PA (US); Rajkumar V. Patil, Keller, TX (US)

(73) Assignee: OKYO Pharma Limited, St. Peter Port (GG)

( * ) Notice: Subject to any disclaimer, the term of this patent is extended or adjusted under 35 U.S.C. 154(b) by 983 days.

(21) Appl. No.: 17/631,032

(22) PCT Filed: Jul. 29, 2020

(86) PCT No.: PCT/US2020/044045
§ 371 (c)(1),
(2) Date: Jan. 28, 2022

(87) PCT Pub. No.: WO2021/021915
PCT Pub. Date: Feb. 4, 2021

(65) Prior Publication Data

US 2022/0267377 A1 Aug. 25, 2022

Related U.S. Application Data

(60) Provisional application No. 62/881,725, filed on Aug. 1, 2019.

(51) Int. Cl.

| | |
|---|---|
| ***A61P 29/00*** | (2006.01) |
| ***A61K 9/00*** | (2006.01) |
| ***A61K 38/00*** | (2006.01) |
| ***A61K 38/10*** | (2006.01) |
| ***A61K 45/06*** | (2006.01) |
| ***A61K 47/54*** | (2017.01) |
| ***A61K 47/60*** | (2017.01) |
| ***C07K 7/08*** | (2006.01) |
| ***C07K 14/47*** | (2006.01) |

(52) U.S. Cl.
CPC .............. *C07K 7/08* (2013.01); *A61K 9/0014* (2013.01); *A61K 38/10* (2013.01); *A61K 45/06* (2013.01); *A61K 47/542* (2017.08); *A61K 47/60* (2017.08); *A61P 29/00* (2018.01)

(58) Field of Classification Search
CPC ...... C07K 7/08; C07K 5/0215; A61K 9/0014; A61K 38/10; A61K 45/06; A61K 47/542; A61K 47/60; A61P 29/00
See application file for complete search history.

(56) References Cited

U.S. PATENT DOCUMENTS

| | | | | |
|---|---|---|---|---|
| 2008/0125357 A1* | 5/2008 | Wittamer | A61P 19/08 435/69.1 |
| 2009/0053831 A1* | 2/2009 | Hornbeck | G01N 33/57484 436/536 |
| 2016/0052982 A1* | 2/2016 | Cohen | A61K 47/543 530/397 |
| 2017/0039314 A1* | 2/2017 | Bremel | G16B 20/20 |
| 2019/0022168 A1 | 1/2019 | Cohen et al. | |

FOREIGN PATENT DOCUMENTS

| | | | |
|---|---|---|---|
| JP | 2010229093 | A | 10/2010 |
| WO | WO-2013117581 | A1 | 8/2013 |
| WO | WO-2014168721 | A2 | 10/2014 |
| WO | WO-2017127827 | A1 | 7/2017 |
| WO | WO-2019001459 | A1 | 1/2019 |

OTHER PUBLICATIONS

Multiple Sclerosis (MS), John Hopkins Medicine, accessed May 13, 2025 at URL hopkinsmedicine.org/health/conditions-and-diseases/multiple-sclerosis-ms#:~: text=Early%20symptoms%20can%20include%20vision, to%20keep%20or%20restore%20functioning, pp. 1-9. (Year: 2025).*
Compston, et al. "Mutliple Sclerosis," The Lancet 359:1221-1231 (2002) (Year: 2002).*
Treatment of pain, Merck Manual, accessed Oct. 14, 2023 at URL merckmanuals.com/professional/neurologic-disorders/pain/treatment, pp. 1-17 (Year: 2023).*
Pain, Merck Manual, accessed Oct. 14, 2023 at URL merckmanuals.com/professional/neurologic-disorders/pain/overview-of-pain, pp. 1-3 (Year: 2023).*
Mattern et al, "Processing, signaling, and physiological function of chemerin," IUBMB Life 66:19-26 (2014) (Year: 2014).*
Diabetic retinopathy, Merck-accessed Jul. 3, 2021 at URL: merckmanuals.com/professional/eye-disorders/retinal-disorders/diabetic-retinopathy?query=ocular neovascular, 5 pages (Year: 2021).*
Lin et al., "dry eye disease: review of diagnostic approaches and treatments," Saudi Journal of ophthalmology 28:173-181 (2014) (Year: 2014).*
Hereditary Optic Neuropathies, Merck Manuals, accessed Mar. 27, 2017 at URL merckmanuals.com/professional/eye-disorders/optic-nerve-disorders/hereditary-optic-neuropathies, pp. 1-2 (Year: 2017).*
Corneal Ulcer, Merck manuals, accessed Sep. 2021 at URL merckmanuals.com/professional/eye-disorders/corneal-disorders/corneal-ulcer (Year: 2021).*

(Continued)

*Primary Examiner* — Julie Ha
*Assistant Examiner* — Kristina M Hellman
(74) *Attorney, Agent, or Firm* — Fenwick & West LLP; Matthew Pavao; Natalie Hendrick

(57) ABSTRACT

The present disclosure relates to peptide compositions and methods for treating an inflammatory condition such as ocular inflammation, retinal inflammation, dry eye, uveitis, allergic conjunctivitis, and inflammation resulting from nerve injury or nerve degeneration. The peptide compositions disclosed herein can also be used for treating pain such as neuropathic pain, ocular pain, chronic pain, pain resulting from chemotherapy or radiation, pain resulting from nerve injury or nerve degeneration, and pain resulting from an inflammatory condition, dysesthesia, or allodynia.

2 Claims, 2 Drawing Sheets

Specification includes a Sequence Listing.

(56) References Cited

OTHER PUBLICATIONS

Neuropathic pain, Merck manuals, accessed May 17, 2025 at URL merckmanuals.com/professional/neurologic-disorders/pain/neuropathic-pain?query=neuropathy, pp. 1-10 (Year: 2025).*

Inflammatory disorders from Merck Manual, pp. 1-4. Accessed Aug. 30, 2020. (Year: 2020).*

Dermatitis from Merck Manual, pp. 1-4. Accessed Aug. 30, 2020. (Year: 2020).*

Inflammation from Merck Manual, pp. 1-3. Accessed Aug. 30, 2020. (Year: 2020).*

Baumgart, "The Diagnosis and Treatment of Crohn's Disease and Ulcerative Colitis," Dtsch Arztebl Int 106(8): 123-33 (2009) (Year: 2009).*

Dafik, L. et al. "Fluorinated Lipid Constructs Permit Facile Passage of Molecular Cargo into Living Cells", J. Am. Chem. Soc., Sep. 2009, 131, 12091-12093.

Doyle, J.R. et al., "Development of a Membrane-anchored Chemerin Receptor Agonist as a Novel Modulator of Allergic Airway Inflammation and Neuropathic Pain", Journal of Biological Chemistry, Mar. 21, 2014, vol. 289, No. 19, pp. 13385-13396.

Schuy S. et al. "Structure and Thermotropic phase Behavior of Fluorinated Phospholipid Bilayers: A combined Attenuated Total Reflection FTIR Spectroscopy and Imaging Ellipsometry Study", J. Phsy. Chem. B, Apr. 2008, 112, 8250-8256.

Shimamura, Ken, et al. "Identification of a stable chemerin analog with potent activity toward ChemR23" Peptides 30 (Jun. 2009); 1529-1538.

Yoder et al. "Nanoscale Patterning in Mixed Fluorocarbon-Hydrocarbon Phospholipid Bilayers", J. Am. Chem. Soc. Jul. 2007, 129, 9037-9043.

* cited by examiner

SEQUENCE LISTING

<160> NUMBER OF SEQ ID NOS: 19

<210> SEQ ID NO 1
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (1)..(1)
<223> OTHER INFORMATION: Xaa at position 1 is alanine, D-alanine, or norvaline
<220> FEATURE:
<221> NAME/KEY: MISC_FEATURE
<222> LOCATION: (2)..(2)
<223> OTHER INFORMATION: Xaa at position 2 is alanine or glycine
<220> FEATURE:
<221> NAME/KEY: MISC_FEATURE
<222> LOCATION: (3)..(3)
<223> OTHER INFORMATION: Xaa at position 2 is phenylalanine or D-tyrosine
<220> FEATURE:
<221> NAME/KEY: MISC_FEATURE
<222> LOCATION: (4)..(4)
<223> OTHER INFORMATION: Xaa at position 2 is phenylalanine or tyrosine
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (7)..(7)
<223> OTHER INFORMATION: Xaa at position 7 is serine or D-serine
<220> FEATURE:
<221> NAME/KEY: MISC_FEATURE
<222> LOCATION: (8)..(8)
<223> OTHER INFORMATION: Xaa at position 8 is glutamine or alpha-aminoadipic acid
<220> FEATURE:
<221> NAME/KEY: MISC_FEATURE
<222> LOCATION: (9)..(9)
<223> OTHER INFORMATION: Xaa at position 9 is tyrosine, phenylalanine, or fluorinated phenylalanine (fF)
<220> FEATURE:
<221> NAME/KEY: MISC_FEATURE
<222> LOCATION: (10)..(10)
<223> OTHER INFORMATION: Xaa at position 10 is alanine or D-alanine
<220> FEATURE:
<221> NAME/KEY: MISC_FEATURE
<222> LOCATION: (11)..(11)
<223> OTHER INFORMATION: Xaa at position 11 is (s)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine or D-serine

<400> SEQUENCE: 1

```
Xaa Xaa Xaa Xaa Xaa Pro Xaa Xaa Xaa Xaa Xaa Xaa
1               5                   10
```

<210> SEQ ID NO 2
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (11)..(11)
<223> OTHER INFORMATION: Xaa at position 11 is (S)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 2

```
Ala Ala Phe Tyr Xaa Pro Ser Gln Tyr Ala Xaa Xaa
1               5                   10
```

<210> SEQ ID NO 3
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (3)..(3)
<223> OTHER INFORMATION: Xaa at position 3 is D-tyrosine
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (7)..(7)
<223> OTHER INFORMATION: Xaa at position 7 is D-serine
<220> FEATURE:

<221> NAME/KEY: MISC_FEATURE
<222> LOCATION: (8)..(8)
<223> OTHER INFORMATION: Xaa at position 8 is alpha-aminoadipic acid
<220> FEATURE:
<221> NAME/KEY: MISC_FEATURE
<222> LOCATION: (11)..(11)
<223> OTHER INFORMATION: Xaa at position 11 is
(S)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 3

```
Ala Gly Xaa Phe Xaa Pro Xaa Xaa Phe Ala Xaa Xaa
1               5                   10
```

<210> SEQ ID NO 4
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (1)..(1)
<223> OTHER INFORMATION: Xaa at position 1 is D-alanine
<220> FEATURE:
<221> NAME/KEY: MISC_FEATURE
<222> LOCATION: (3)..(3)
<223> OTHER INFORMATION: Xaa at position 3 is D-tyrosine
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (7)..(7)
<223> OTHER INFORMATION: Xaa at position 7 is D-serine
<220> FEATURE:
<221> NAME/KEY: MISC_FEATURE
<222> LOCATION: (9)..(9)
<223> OTHER INFORMATION: Xaa at position 9 is fluorinated phenylalanine
<220> FEATURE:
<221> NAME/KEY: MISC_FEATURE
<222> LOCATION: (10)..(10)
<223> OTHER INFORMATION: Xaa at position 10 is D-alanine
<220> FEATURE:
<221> NAME/KEY: MISC_FEATURE
<222> LOCATION: (11)..(11)
<223> OTHER INFORMATION: Xaa at position 11 is
(S)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 4

```
Xaa Gly Xaa Phe Xaa Pro Xaa Gln Xaa Xaa Xaa Xaa
1               5                   10
```

<210> SEQ ID NO 5
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (1)..(1)
<223> OTHER INFORMATION: Xaa at position 1 is norvaline
<220> FEATURE:
<221> NAME/KEY: MISC_FEATURE
<222> LOCATION: (3)..(3)
<223> OTHER INFORMATION: Xaa at position 3 is D-tyrosine -continued

```
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (7)..(7)
<223> OTHER INFORMATION: Xaa at position 7 is D-serine
<220> FEATURE:
<221> NAME/KEY: MISC_FEATURE
<222> LOCATION: (10)..(10)
<223> OTHER INFORMATION: Xaa at position 10 is D-alanine
<220> FEATURE:
<221> NAME/KEY: MISC_FEATURE
<222> LOCATION: (11)..(11)
<223> OTHER INFORMATION: Xaa at position 11 is
      (S)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 5

Xaa Gly Xaa Phe Xaa Pro Xaa Gln Phe Xaa Xaa Xaa
1               5                   10


<210> SEQ ID NO 6
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (3)..(3)
<223> OTHER INFORMATION: Xaa at position 3 is D-tyrosine
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (7)..(7)
<223> OTHER INFORMATION: Xaa at position 7 is D-serine
<220> FEATURE:
<221> NAME/KEY: MISC_FEATURE
<222> LOCATION: (11)..(11)
<223> OTHER INFORMATION: Xaa at position 11 is
      (S)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-serine

<400> SEQUENCE: 6

Ala Gly Xaa Phe Xaa Pro Xaa Gln Phe Ala Xaa Xaa
1               5                   10


<210> SEQ ID NO 7
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (1)..(1)
<223> OTHER INFORMATION: Xaa at position 1 is D-alanine
<220> FEATURE:
<221> NAME/KEY: MISC_FEATURE
<222> LOCATION: (3)..(3)
<223> OTHER INFORMATION: Xaa at position 3 is D-tyrosine
<220> FEATURE:
<221> NAME/KEY: MISC_FEATURE
<222> LOCATION: (5)..(5)
```

-continued

<223> OTHER INFORMATION: Xaa at position 5 is norleucine
<220> FEATURE:
<221> NAME/KEY: MISC_FEATURE
<222> LOCATION: (7)..(7)
<223> OTHER INFORMATION: Xaa at position 7 is D-serine
<220> FEATURE:
<221> NAME/KEY: MISC_FEATURE
<222> LOCATION: (10)..(10)
<223> OTHER INFORMATION: Xaa at position 10 is D-alanine
<220> FEATURE:
<221> NAME/KEY: MISC_FEATURE
<222> LOCATION: (11)..(11)
<223> OTHER INFORMATION: Xaa at position 11 is
(S)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 7

```
Xaa Gly Xaa Phe Xaa Pro Xaa Gln Phe Xaa Xaa Xaa
1               5                   10
```

<210> SEQ ID NO 8
<211> LENGTH: 163
<212> TYPE: PRT
<213> ORGANISM: Homo sapiens

<400> SEQUENCE: 8

```
Met Arg Arg Leu Leu Ile Pro Leu Ala Leu Trp Leu Gly Ala Val Gly
1               5                   10                  15

Val Gly Val Ala Glu Leu Thr Glu Ala Gln Arg Arg Gly Leu Gln Val
            20                  25                  30

Ala Leu Glu Glu Phe His Lys His Pro Pro Val Gln Trp Ala Phe Gln
        35                  40                  45

Glu Thr Ser Val Glu Ser Ala Val Asp Thr Pro Phe Pro Ala Gly Ile
    50                  55                  60

Phe Val Arg Leu Glu Phe Lys Leu Gln Gln Thr Ser Cys Arg Lys Arg
65                  70                  75                  80

Asp Trp Lys Lys Pro Glu Cys Lys Val Arg Pro Asn Gly Arg Lys Arg
                85                  90                  95

Lys Cys Leu Ala Cys Ile Lys Leu Gly Ser Glu Asp Lys Val Leu Gly
            100                 105                 110

Arg Leu Val His Cys Pro Ile Glu Thr Gln Val Leu Arg Glu Ala Glu
        115                 120                 125

Glu His Gln Glu Thr Gln Cys Leu Arg Val Gln Arg Ala Gly Glu Asp
    130                 135                 140

Pro His Ser Phe Tyr Phe Pro Gly Gln Phe Ala Phe Ser Lys Ala Leu
145                 150                 155                 160

Pro Arg Ser
```

<210> SEQ ID NO 9
<211> LENGTH: 137
<212> TYPE: PRT
<213> ORGANISM: Homo sapiens

<400> SEQUENCE: 9

```
Glu Leu Thr Glu Ala Gln Arg Arg Gly Leu Gln Val Ala Leu Glu Glu
1               5                   10                  15

Phe His Lys His Pro Pro Val Gln Trp Ala Phe Gln Glu Thr Ser Val
            20                  25                  30

Glu Ser Ala Val Asp Thr Pro Phe Pro Ala Gly Ile Phe Val Arg Leu
```

-continued

```
        35                  40                  45

Glu Phe Lys Leu Gln Gln Thr Ser Cys Arg Lys Arg Asp Trp Lys Lys
    50                  55                  60

Pro Glu Cys Lys Val Arg Pro Asn Gly Arg Lys Arg Lys Cys Leu Ala
65                  70                  75                  80

Cys Ile Lys Leu Gly Ser Glu Asp Lys Val Leu Gly Arg Leu Val His
                85                  90                  95

Cys Pro Ile Glu Thr Gln Val Leu Arg Glu Ala Glu Glu His Gln Glu
            100                 105                 110

Thr Gln Cys Leu Arg Val Gln Arg Ala Gly Glu Asp Pro His Ser Phe
        115                 120                 125

Tyr Phe Pro Gly Gln Phe Ala Phe Ser
    130                 135


<210> SEQ ID NO 10
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (3)..(3)
<223> OTHER INFORMATION: Xaa at position 3 is D-tyrosine
<220> FEATURE:
<221> NAME/KEY: MISC_FEATURE
<222> LOCATION: (7)..(7)
<223> OTHER INFORMATION: Xaa at position 7 is D-serine
<220> FEATURE:
<221> NAME/KEY: MISC_FEATURE
<222> LOCATION: (10)..(10)
<223> OTHER INFORMATION: Xaa at position 10 is D-alanine
<220> FEATURE:
<221> NAME/KEY: MISC_FEATURE
<222> LOCATION: (11)..(11)
<223> OTHER INFORMATION: Xaa at position 10 is
      (s)-1,2,3,4-tetrahydroisoquinoline-3-carboxylic acid

<400> SEQUENCE: 10

Gly Gly Xaa Phe Leu Pro Xaa Gln Phe Xaa Xaa Ser
1               5                   10


<210> SEQ ID NO 11
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (11)..(11)
<223> OTHER INFORMATION: Xaa at position 11 is
      (s)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 11

Ala Ala Tyr Phe Xaa Pro Ser Gln Phe Ala Xaa Xaa
1               5                   10


<210> SEQ ID NO 12
<211> LENGTH: 12
```

-continued

```
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (11)..(11)
<223> OTHER INFORMATION: Xaa at position 11 is
      (s)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 12

Ala Gly Tyr Phe Xaa Pro Thr Asn Phe Ala Xaa Xaa
1               5                   10


<210> SEQ ID NO 13
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (11)..(11)
<223> OTHER INFORMATION: Xaa at position 11 is
      (s)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 13

Ala Ala Phe Tyr Xaa Pro Thr Gln Phe Ala Xaa Xaa
1               5                   10


<210> SEQ ID NO 14
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (10)..(10)
<223> OTHER INFORMATION: Xaa at position 10 is D-alanine
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 14

Ala Ala Tyr Phe Xaa Pro Ser Gln Tyr Xaa Phe Xaa
1               5                   10


<210> SEQ ID NO 15
<211> LENGTH: 12
<212> TYPE: PRT
<213> ORGANISM: Artificial Sequence
```

-continued

<220> FEATURE:
<223> OTHER INFORMATION: Artificial peptide composition
<220> FEATURE:
<221> NAME/KEY: MISC_FEATURE
<222> LOCATION: (3)..(3)
<223> OTHER INFORMATION: Xaa at position 3 is D-tyrosine
<220> FEATURE:
<221> NAME/KEY: MISC_FEATURE
<222> LOCATION: (5)..(5)
<223> OTHER INFORMATION: Xaa at position 5 is D-norleucine
<220> FEATURE:
<221> NAME/KEY: MISC_FEATURE
<222> LOCATION: (7)..(7)
<223> OTHER INFORMATION: Xaa at position 7 is D-serine
<220> FEATURE:
<221> NAME/KEY: MISC_FEATURE
<222> LOCATION: (10)..(10)
<223> OTHER INFORMATION: Xaa at position 10 is D-alanine
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 15

Ala Gly Xaa Tyr Xaa Pro Xaa Gln Phe Xaa Phe Xaa
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (1)..(1)
<223> OTHER INFORMATION: Xaa at position 1 is D-alanine
<220> FEATURE:
<221> NAME/KEY: MISC_FEATURE
<222> LOCATION: (3)..(3)
<223> OTHER INFORMATION: Xaa at position 3 is D-tyrosine
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (7)..(7)
<223> OTHER INFORMATION: Xaa at position 7 is D-serine
<220> FEATURE:
<221> NAME/KEY: MISC_FEATURE
<222> LOCATION: (8)..(8)
<223> OTHER INFORMATION: Xaa at position 8 is alpha-aminoadipic acid
<220> FEATURE:
<221> NAME/KEY: MISC_FEATURE
<222> LOCATION: (10)..(10)
<223> OTHER INFORMATION: Xaa at position 10 is D-alanine
<220> FEATURE:
<221> NAME/KEY: MISC_FEATURE
<222> LOCATION: (11)..(11)
<223> OTHER INFORMATION: Xaa at position 11 is
      (s)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 16

Xaa Gly Xaa Tyr Xaa Pro Xaa Xaa Phe Xaa Xaa Xaa
1               5                   10

<210> SEQ ID NO 17
<211> LENGTH: 12
<212> TYPE: PRT
<213> ORGANISM: Artificial Sequence

```
<220> FEATURE:
<223> OTHER INFORMATION: Artificial peptide composition
<220> FEATURE:
<221> NAME/KEY: MISC_FEATURE
<222> LOCATION: (1)..(1)
<223> OTHER INFORMATION: Xaa at position 1 is D-alanine
<220> FEATURE:
<221> NAME/KEY: MISC_FEATURE
<222> LOCATION: (3)..(3)
<223> OTHER INFORMATION: Xaa at position 3 is D-tyrosine
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (7)..(7)
<223> OTHER INFORMATION: Xaa at position 7 is D-serine
<220> FEATURE:
<221> NAME/KEY: MISC_FEATURE
<222> LOCATION: (8)..(8)
<223> OTHER INFORMATION: Xaa at position 8 is alpha-aminoadipic acid
<220> FEATURE:
<221> NAME/KEY: MISC_FEATURE
<222> LOCATION: (10)..(10)
<223> OTHER INFORMATION: Xaa at position 10 is D-alanine
<220> FEATURE:
<221> NAME/KEY: MISC_FEATURE
<222> LOCATION: (11)..(11)
<223> OTHER INFORMATION: Xaa at position 11 is
      (s)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 17

Xaa Gly Xaa Phe Xaa Pro Xaa Xaa Phe Xaa Xaa Xaa
1               5                   10


<210> SEQ ID NO 18
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (5)..(5)
<223> OTHER INFORMATION: Xaa at position 5 is norleucine
<220> FEATURE:
<221> NAME/KEY: MISC_FEATURE
<222> LOCATION: (11)..(11)
<223> OTHER INFORMATION: Xaa at position 11 is
      (s)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-alanine

<400> SEQUENCE: 18

Ala Gly Phe Phe Xaa Pro Ser Gln Phe Ala Xaa Xaa
1               5                   10


<210> SEQ ID NO 19
<211> LENGTH: 12
<212> TYPE: PRT
<213> ORGANISM: Artificial Sequence
<220> FEATURE:
<223> OTHER INFORMATION: Artificial peptide composition
<220> FEATURE:
<221> NAME/KEY: MISC_FEATURE
<222> LOCATION: (5)..(5)
<223> OTHER INFORMATION: Xaa at position 5 is norleucine
<220> FEATURE:
```

-continued

```
<221> NAME/KEY: MISC_FEATURE
<222> LOCATION: (11)..(11)
<223> OTHER INFORMATION: Xaa at position 11 is
      (s)-1,2,3,4-tetrahydroisoquinoline-3-carboxylic acid
<220> FEATURE:
<221> NAME/KEY: MISC_FEATURE
<222> LOCATION: (12)..(12)
<223> OTHER INFORMATION: Xaa at position 12 is D-serine

<400> SEQUENCE: 19

Gly Gly Phe Phe Xaa Pro Ser Gln Phe Ala Xaa Xaa
1               5                   10
```

COMPOSITIONS COMPRISING CHEMERIN ANALOGS AND METHODS OF USE

RELATED APPLICATIONS

This application is a National Stage Application, filed under 35 U.S.C. 371 of International Application No. PCT/US2020/044045, filed on Jul. 29, 2020, which claims priority to, and the benefit of, U.S. Ser. No. 62/881,725, filed on Aug. 1, 2019, the contents of which are incorporated herein by reference in their entireties.

INCORPORATION BY REFERENCE OF SEQUENCE LISTING

The contents of the text file named "OKYO_006_N01US Sequence Listing.txt", which was created on Jan. 28, 2022 and is about 16 KB in size, are hereby incorporated by reference in their entireties.

TECHNICAL FIELD

The present disclosure relates generally to chemerin analogs and their use in treating various diseases and conditions including but not limited to, inflammatory conditions and pain conditions.

BACKGROUND OF TIE DISCLOSURE

There is a variety of inflammatory conditions including, but not limited to, ocular inflammation, dry eye, uveitis (e.g., noninfectious uveitis), allergic conjunctivitis, retinal inflammation, and inflammation resulting from nerve injury or nerve degeneration. Ocular inflammation can be caused by a microbial infection of the eye. Such infection may be fungal, viral, or bacterial. Ocular inflammation can also be caused by trauma, autoimmune disease, chemical injury, contact lens, or other external stimuli.

For example, dry eye is a multifactorial disease of the tears and the ocular surface with inflammation playing a part in its pathogenesis. Dry eye is a common and often chronic problem, particularly in older adults. In 2000, its prevalence in the US has been estimated around 17% in females and 12% in males but it has been increased in recent years and estimated to be more than 50%. People with dry eyes either do not produce enough tears or their tears are of poor quality. Tears are produced by several glands in and around the eyelids. Tear production tends to diminish with age, with various medical conditions or as a side effect of certain medicines, Environmental conditions, such as wind and dry climates, can also decrease tear volume due to increased tear evaporation. When the normal amount of tear production decreases or tears evaporate too quickly from the eyes, symptoms of dry eye can develop. As for the quality of tears, tears are made up of three layers: oil, water and mucus. Each component protects and nourishes the front surface of the eye. A smooth oil layer helps prevent evaporation of the water layer, while the mucin layer spreads the tears evenly over the surface of the eye. If the tears evaporate too quickly or do not spread evenly over the cornea due to deficiencies with any of the three tear layers, dry eye symptoms can develop.

The common form of dry eyes occurs when the water layer of tears is inadequate. This condition is also called keratoconjunctivitis sicca (KCS).

There is also a variety of pain conditions including neuropathic pain, ocular pain, chronic pain, pain resulting from chemotherapy or radiation, pain resulting from nerve injury or nerve degeneration, and pain resulting from an inflammatory condition, dysesthesia, or allodynia.

For example, neuropathic pain is a complex, chronic pain state that usually is accompanied by tissue injury. With neuropathic pain, the nerve fibers themselves might be damaged, dysfunctional, or injured. These damaged nerve fibers send incorrect signals to other pain centers. The impact of a nerve fiber injury includes a change in nerve function both at the site of injury and areas around the injury. Neuropathic pain is a serious health problem that affects millions of people worldwide and occurs in as much as 7% of the general population. The management of neuropathic pain in patients is complex with an estimated 40-60% of individuals refractive to existing analgesic therapies. The aging population, the diabetes epidemic, and patients with cancer and AIDS all contribute to the prevalence of intractable neuropathic pain, highlighting the pressing need to develop novel therapeutics for this condition.

The eye is heavily innervated by sensory nerve fibers, and inflammatory, ischemic, and even neoplastic involvement of the eye and orbit can produce pain. Ophthalmic causes of eye pain include dry eyes and other forms of keratitis, acute angle-closure glaucoma, and intraocular inflammation. Keratitis sicca, or dry eye, is a very common cause of ophthalmic discomfort. These conditions are most commonly diagnosed through examination of the cornea, anterior segment, and anterior vitreous by slit lamp. Exacerbated by visual tasks that decrease blink frequency, especially work on the computer, it has various causes and results from conditions that either decrease tear production or increase tear evaporation. Dry eye is one of the characteristic features of the autoimmune Sjögren syndrome. Evidence of fluorescein or rose bengal staining, abnormal tear breakup time, or decreased Schirmer test may help confirm dry eye syndrome. Posterior segment examination with indirect ophthalmoscopy or slit-lamp bionicroscopy may reveal evidence of choroidal or retinal inflammation or posterior scleritis.

Chemotherapy or radiation can cause peripheral neuropathy (painful numbness of the extremities), or paresthesia (numbness and tingling of hands, feet or any extremity of the body).

The present disclosure addresses the need of patients suffering from various pain and/or inflammatory conditions such as those stated above.

SUMMARY OF THE DISCLOSURE

The present disclosure provides compositions and methods for treating or ameliorating at least one symptom of neuropathic pain, ocular pain, chronic pain, pain resulting from chemotherapy or radiation, pain resulting from nerve injury or nerve degeneration, pain resulting from an inflammatory condition, dysesthesia, or allodynia, inflammation resulting from nerve injury or nerve degeneration, ocular inflammation, retinal inflammation, uveitis, allergic conjunctivitis, and/or dry eye.

In one aspect, the present disclosure provides a composition comprising: a peptide comprising amino acids having a sequence of $X_1X_2X_3X_4$-Nle-$PX_5X_6X_7X_8$-Tic-$X_9$ (SEQ ID NO: 1), and a lipid entity linked to the peptide, wherein: $X_1$ is selected from A, dA, and NorV; $X_2$ is A or G; $X_3$ is F or dY; $X_4$ is F or Y; $X_5$ is S or dS; $X_6$ is Q or α-aminoadipic acid (Aad); $X_7$ is selected from Y, F, and fF; $X_8$ is A or dA; Tic is (S)-1,2,3,4-tetrahydroisoquinoline-3-carboxylic acid; and $X_9$ is dA or dS.

In some embodiments, the peptide consists of amino acids having the sequence of $X_1X_2X_3X_4$-Nle-$PX_5X_6X_7X_8$-Tic-$X_9$ (SEQ ID NO: 1).

In some embodiments, the peptide is selected from AAFY-Nle-PSQYA-Tic-dA (SEQ ID NO: 2), AG-dY-F-Nle-P-dS-Aad-FA-Tic-dA (SEQ ID NO: 3), dA-G-dY-F-Nle-P-dS-Q-fF-dA-Tic-dA (SEQ ID NO: 4), NorV-G-dY-F-Nle-P-dS-QF-dA-Tic-dA (SEQ ID NO: 5), AG-dY-F-Nle-P-dS-QFA-Tic-dS (SEQ ID NO: 6), and dA-G-dY-F-Nle-P-dS-QF-dA-Tic-dA (SEQ ID NO: 7).

In some embodiments, the lipid entity is linked to the peptide through a linker entity.

In some embodiments, the lipid entity is linked at or near the N-terminus of the peptide.

In some embodiments, the lipid entity is linked at or near the C-terminus of the peptide.

In some embodiments, the lipid entity is selected from the group consisting of α-linolenic acid, γ-linolenic acid, stearidonic acid, eicosapentaenoic acid, docosahexaenoic acid, linoleic acid, dihomo-γ-linolenic acid, arachidonic acid, docosatetraenoic acid, palmitoleic acid, vaccenic acid, paullinic acid, oleic acid, elaidic acid, gondoic acid, erucic acid, nervonic acid, mead acid, nyristic acid, palmitic acid, stearic acid, 1,2-dipalmitoyl-sn-glycero-3-phosphoethanolamine (DPPE), GM1 ganglioside, GM2 ganglioside, GM3 ganglioside, 1,2-dipalmitoyl-sn-glycero-3-phosphocholine (DPPC), 1,2-dioleoyl-sn-glycero-3-phospho-L-serine (DOPS), 1,2-dioleoyl-sn-glycero-3-phosphocholine (DOPC), a glycosphingolipid, a sphingolipid, phosphatidylinositol 4,5-Lisphosphate (PIP2), a ceramide, cholesterol, ergosterol, phytosterol, a hopanoid, a steroid, and 17-carboxy-1-oxo-heptadecyl.

In some embodiments, the lipid entity is selected from the group consisting of α-linolenic acid, γ-linolenic acid, palmitic acid, myristic acid, vaccenic acid, oleic acid, and elaidic acid.

In some embodiments, the linker entity comprises ethylene glycol, polyethylene glycol, a peptide, aminoethylethanolamine (AEEA), inulin, a trisaccharide, or a combination thereof.

In some embodiments, the linker entity comprises polyethylene glycol (PEG).

In some embodiments, the linker entity is selected from the group consisting of:

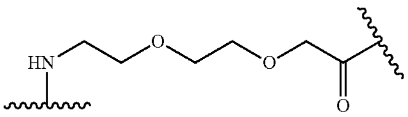

OEG

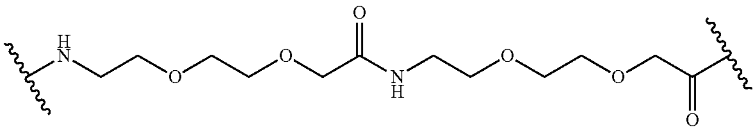

2xOEG

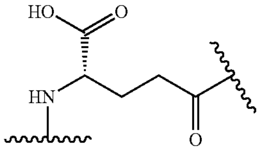

γGlu

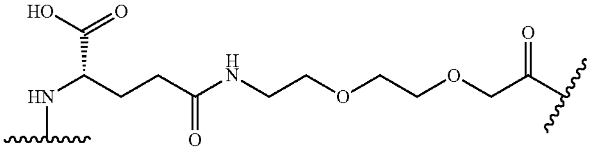

γGlu-OEG

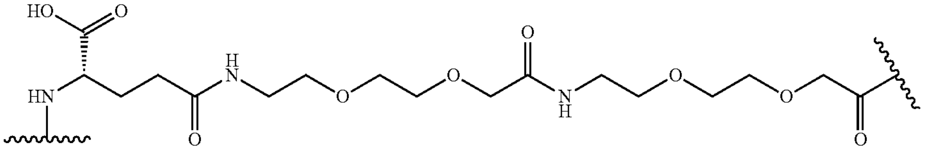

γGlu-2xOEG

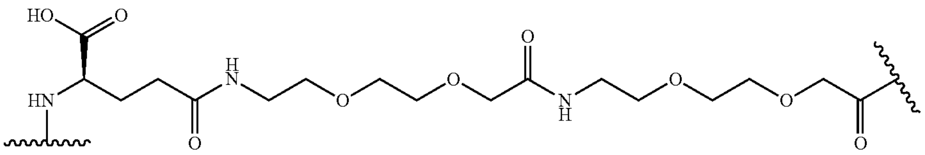

DγGlu-2xOEG

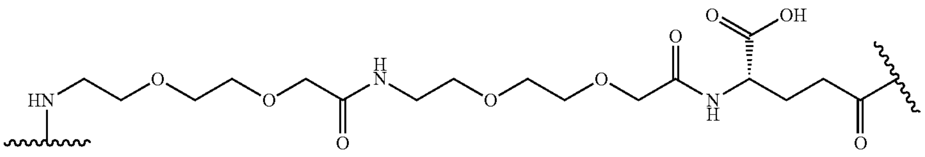

2xOEG-γGlu

-continued
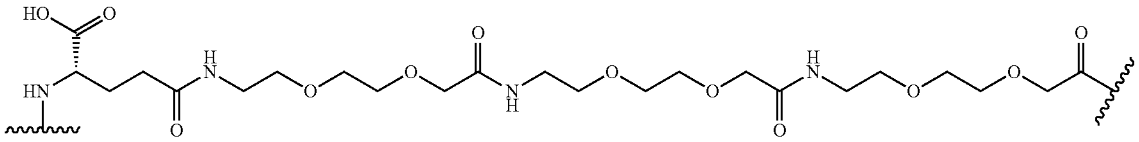
γGlu-3xOEG
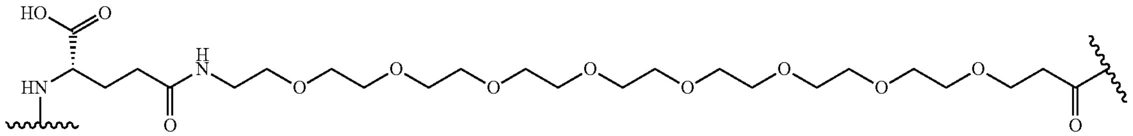
γGlu-8PEG
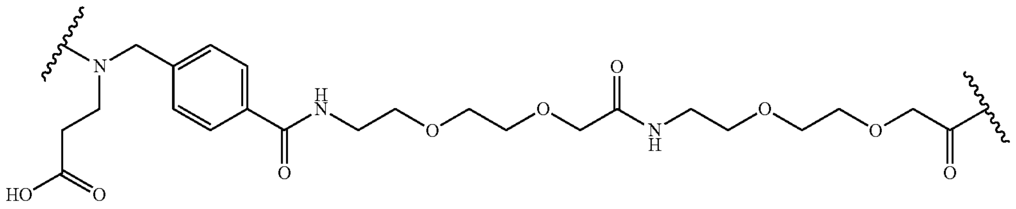
benzyl-βAla-2xOEG
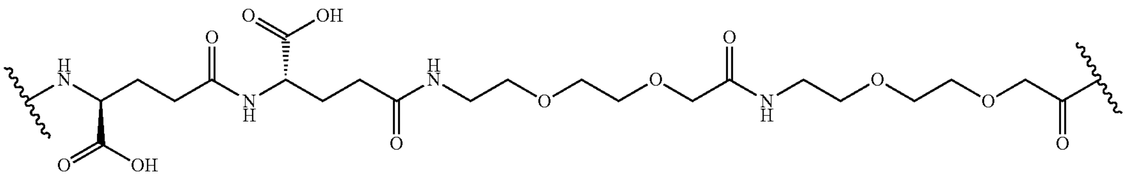
2xγGlu-2xOEG
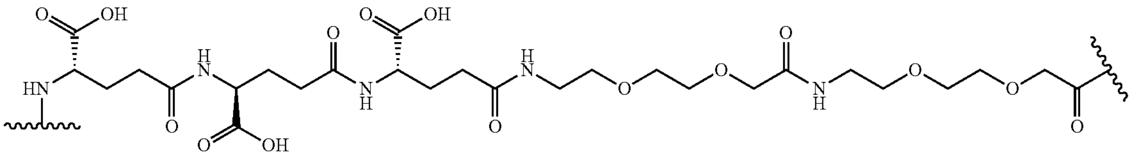
3xγGlu-2xOEG
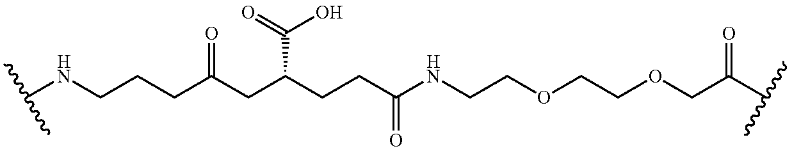
Abu-γGlu-OEG
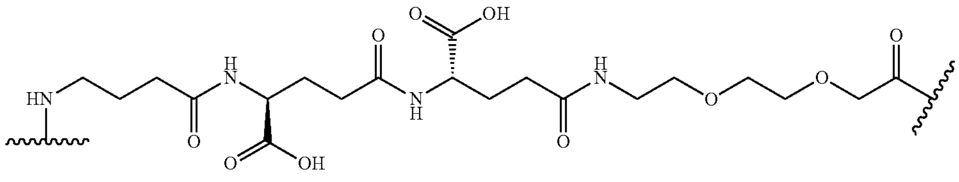
Abu-2xγGlu-OEG
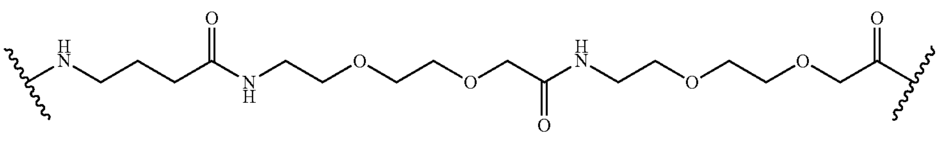
Abu-2xOEG In some embodiments, a combination of the lipid entity and the linker entity comprises palmitic acid-PEGS.

In some embodiments, the lipid entity is linked to the peptide covalently.

In some embodiments, the composition is soluble in water.

In one aspect, the present disclosure relates to a pharmaceutical composition comprising the peptide composition described herein and a pharmaceutically acceptable carrier.

In one aspect, the present disclosure relates to a method of treating pain in a subject in need thereof, comprising administering to the subject a therapeutically effective amount of the peptide composition or the pharmaceutical composition described herein.

In some embodiments, the pain is ocular pain, chronic pain, neuropathic pain, pain resulting from chemotherapy or radiation, pain resulting from nerve injury or nerve degeneration, or pain resulting from an inflammatory condition, dysesthesia, or allodynia.

In some embodiments, the peptide composition or the pharmaceutical composition is administered topically.

In some embodiments, the peptide composition or the pharmaceutical composition is administered once a day, twice a day, or thrice a day.

In some embodiments, the subject is a human.

Any aspect or embodiment described herein can be combined with any other aspect or embodiment as disclosed herein. While the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

(SEQ ID NO: 10)

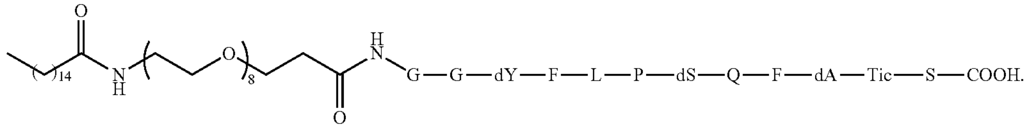

In some embodiments, the method further comprises administering an analgesic agent (e.g., paracetamol, a non-steroidal anti-inflammatory drug, a COX-2 inhibitor, an opioid, or medical *cannabis*).

In some embodiments, the subject is a human.

Figure 2:
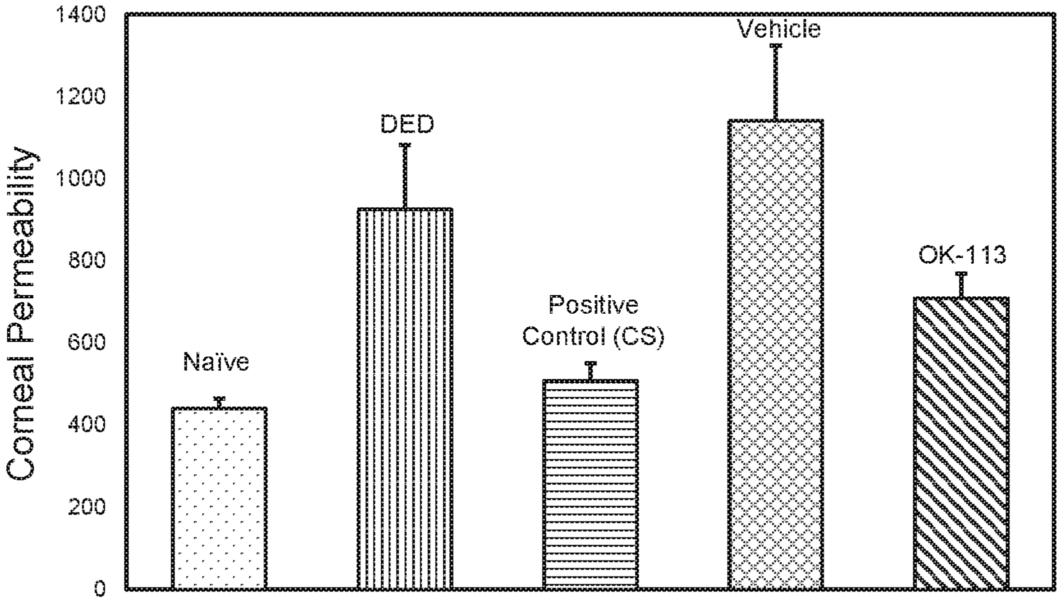

FIG. 2 is a graph showing that increase in corneal permeability due to dry eye was reduced significantly OK-113. Potency of OK-113 was comparable to cyclosporine (CS), an active ingredient of Restasis® (Allergan). The animal study was done with single dose. OK-113 has the following structure:

(SEQ ID NO: 5)

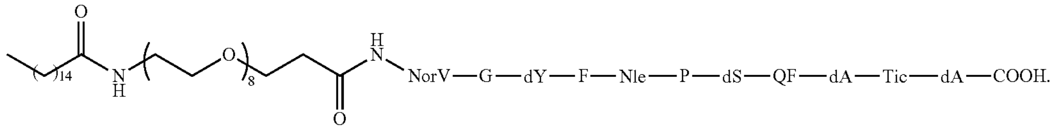

In another aspect, the present disclosure relates to a method of treating an inflammatory condition in a subject in need thereof, comprising administering to the subject a therapeutically effective amount of the peptide composition or the pharmaceutical composition described herein.

In some embodiments, the inflammatory condition is ocular inflammation.

In some embodiments, the inflammatory condition is dry eye disease, uveitis (e.g., noninfectious uveitis), allergic conjunctivitis, or retinal inflammatory disease.

In some embodiments, the inflammatory condition is resulting from nerve injury or nerve degeneration.

In some embodiments, the peptide composition or the pharmaceutical composition is administered topically.

In some embodiments, the peptide composition or the pharmaceutical composition is administered once a day, twice a day, or thrice a day.

Figure 3:
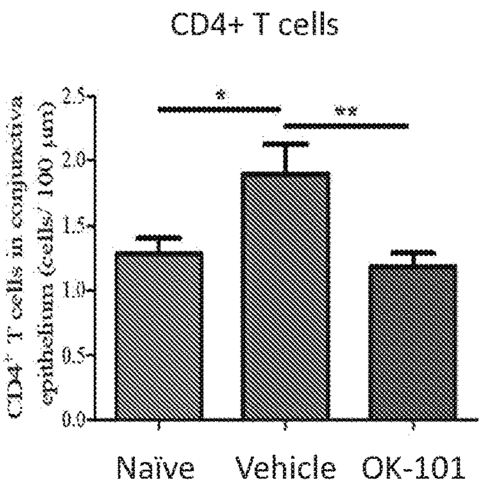

FIG. 3 is a graph showing that OK-101 significantly reduced the dry eye induced $CD4^+$ T-cells infiltration, which are known biomarkers of inflammation.

Figure 4:
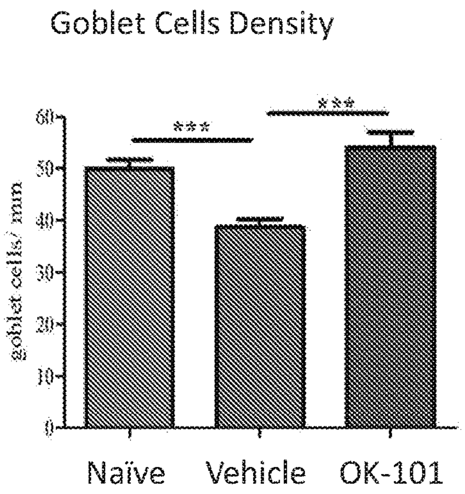

FIG. 4 is a graph showing that OK-101 normalized the dry eye induced loss of goblet cell density.

Figure 5:
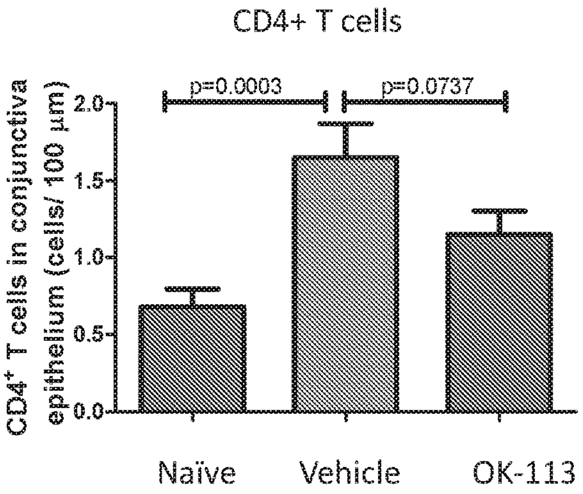

FIG. 5 is a graph showing that OK-113 significantly reduced the dry eye induced $CD4^+$ T-cells infiltration.

Figure 6:
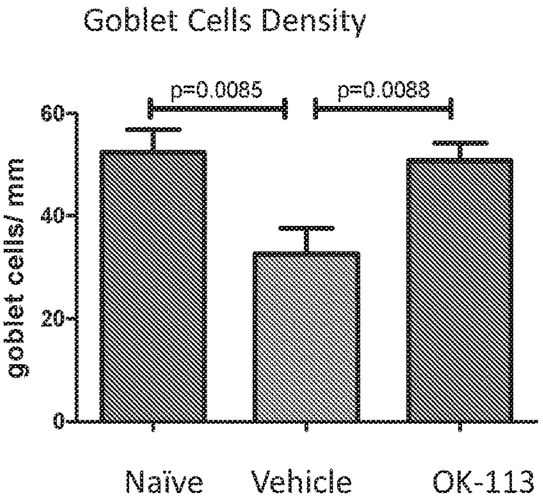

FIG. 6 is a graph showing that OK-113 normalized the dry eye induced loss of goblet cell density.

DETAILED DESCRIPTION OF THE DISCLOSURE

As described in further detail herein, there is an unmet need for novel strategies to treat pain, in particular neuropathic pain, a disease which affects millions of people worldwide and occurs in as much as 7% of the population.

The management of patients with neuropathic pain is complex, with many patients not responding to treatment or only experiencing partial relief. At the extreme, there is a substantial subpopulation with moderate to severe chronic refractory pain where there is an urgent need for more effective, long acting therapeutics.

CMKLR1 is a G protein-coupled receptor which has been shown to modulate nociception. This receptor is expressed in glia, dorsal root ganglion neurons, and immune cells. The endogenous ligand (agonist) for CMKLR1 is chemerin, a 163 amino acid protein Chemerin, also known as retinoic acid receptor responder protein 2 (RARRES2), tazarotene-induced gene 2 protein (TIG2), or RAR-responsive protein TIG2, is a protein that in humans is encoded by the RARRES2 gene. The *Homo sapiens*' amino acid sequence of chemerin is shown below in SEQ ID NO: 8.

```
NCBI Reference Sequence: NP_002880.1
                                        (SEQ ID NO: 8)
MRRLLIPLAL WLGAVGVGVA ELTEAQRRGL QVALEEFHKH

PPVQWAFQET SVESAVDTPF PAGIFVRLEF KLQQTSCRKR

DWKKPECKVR PNGRKRKCLA CIKLGSEDKV LGRLVHCPIE

TQVLREAEEH QETQCLRVQR AGEDPHSFYF PGQFAFSKAL

PRS.
```

Chemerin is inactive as pre-prochemerin (having SEQ ID NO: 8) and is activated through cleavage of the C-terminus and N-terminus to form a chemerin fragment having an amino acid sequence from position 21 to 157 of SEQ ID NO: 8, which can function as an agonist for CMKLR1 This chemerin fragment has the following amino acid sequence:

```
                                        (SEQ ID NO: 9)
ELTEAQRRGL QVALEEFHKH PPVQWAFQET SVESAVDTPF

PAGIFVRLEF KLQQTSCRKR DWKKPECKVR PNGRKRKCLA

CIKLGSEDKV LGRLVHCPIE TQVLREAEEH QETQCLRVQR

AGEDPHSFYF PGQFAFS.
```

Among other things, the present disclosure provides a composition comprising a chemerin analog that can retain some or all of the biological functions of the amino acid sequence of SEQ ID NO: 9, e.g., functioning as an agonist of CMKLR1. The chemerin analog can be an analog of either the full length or a fragment of chemerin.

In one aspect, the present disclosure provides a composition comprising: a peptide comprising amino acids having a sequence of $X_1X_2X_3X_4$-Nle-$PX_5X_6X_7X_8$-Tic-$X_9$ (SEQ ID NO: 1), and a lipid entity linked to the peptide. In some embodiments, any one or more than one of the amino acids in the peptide can be either an L-amino acid or a D-amino acid. In some embodiments, any one or more than one of the amino acids in the peptide can be fluorinated. As used herein, a fluorinated amino acid is an amino acid in which one or more hydrogen is replaced by a fluorine. As used herein, Nle refers to norleucine; and Tic refers to (S)-1,2,3,4-tetrahydroisoquinoline-3-carboxylic acid.

In some embodiments, $X_1$ is selected from A, dA, and NorV; $X_2$ is A or G; $X_3$ is F or dY; $X_4$ is F or Y; $X_5$ is S or dS; $X_6$ is Q or $\alpha$-aminoadipic acid (Aad); $X_7$ is selected from Y, F, and fF; $X_8$ is A or dA; and $X_9$ is dA or dS.

As used herein, NorV refers to norvaline.

As used herein, a lowercase d in front of an amino acid denotes a D-amino acid of that amino acid. For example, dA denotes D-alanine; dY denotes D-tyrosine; and dS denotes D-serine.

As used herein, a lowercase f in front of an amino acid denotes that the amino acid is fluorinated. For example, f denotes fluorinated phenylalanine.

In some embodiments, the peptide has no more than 20 amino acids, no more than 19 amino acids, no more than 18 amino acids, no more than 17 amino acids, no more than 16 amino acids, no more than 15 amino acids, no more than 14 amino acids, no more than 13 amino acids, or no more than 12 amino acids.

In some embodiments, the peptide has at least 9 amino acids, at least 10 amino acids, at least 11 amino acids, or at least 12 amino acids.

Combinations of the above-referenced ranges for the number of amino acids are also possible. For example, the peptide can have about 9 to 20 amino acid, about 10 to 20 amino acids, or about 10 to 18 amino acids.

In some embodiments, the peptide consists of amino acids having the sequence of $X_1X_2X_3X_4$-Nle-$PX_5X_6X_7X_8$-Tic-$X_9$ (SEQ ID NO: 1).

In some embodiments, the peptide comprises AAFY-Nle-PSQYA-Tic-dA (SEQ ID NO: 2), AG-dY-F-Nle-P-dS-Aad-FA-Tic-dA (SEQ ID NO: 3), dA-G-dY-F-Nle-P-dS-Q-fF-dA-Tic-dA (SEQ ID NO: 4), NorV-G-dY-F-Nle-P-dS-QF-dA-Tic-dA (SEQ ID NO: 5), AG-dY-F-Nle-P-dS-QFA-Tic-dS (SEQ ID NO: 6), or dA-G-dY-F-Nle-P-dS-QF-dA-Tic-dA (SEQ ID NO: 7).

In some embodiments, the peptide consists of AAFY-Nle-PSQYA-Tic-dA (SEQ ID NO: 2), AG-dY-F-Nle-P-dS-Aad-FA-Tic-dA (SEQ ID NO: 3), dA-G-dY-F-Nle-P-dS-Q-fF-dA-Tic-dA (SEQ ID NO: 4), NorV-G-dY-F-Nle-P-dS-QF-dA-Tic-dA (SEQ ID NO: 5), AG-dY-F-Nle-P-dS-QFA-Tic-dS (SEQ ID NO: 6), or dA-G-dY-F-Nle-P-dS-QF-dA-Tic-dA (SEQ ID NO: 7).

Any of a variety of lipid entities may be utilized in accordance with the present disclosure. According to various embodiments, a lipid entity can comprise an entity capable of insertion into a lipid bilayer (e.g., a cell membrane). In some embodiments, a lipid entity is capable of incorporating into a lipid raft in a lipid bilayer (e.g., a cell membrane).

In some embodiments, the lipid entity can comprise a saturated or unsaturated fatty acid. The numbers in the lipid name are used to describe the fatty acid chains on the lipid. The numbers are generally presented in the format (number of carbons in fatty acid chain):(number of double bonds in fatty acid chain), e.g., 16:0 would be 16 carbons in the fatty acid chain with zero double bonds. The saturated or unsaturated fatty acid can include at least 4 carbons, at least 5 carbons, at least 6 carbons, at least 7 carbons, at least 8 carbons, at least 9 carbons, at least 10 carbons, or at least 15 carbons in the fatty acid chain. In some embodiments, the saturated or unsaturated fatty acid can include about 4-24 carbons in the fatty acid chain. The number of double bonds in the fatty acid chain can be in the range of 0-10, e.g., 0-8, 0-6, 1-8, 1-6. For example, the lipid entity can be C22:0, C22:1, C22:2, C22:3, C22:4, C22:5, C22:6, C20:0, C20:1, C20:2, C20:3, C20:4, C20:5, C20:6, C18:0, C18:1, C18:2, C18:3, C18:4, C18:5, C18:6, C10:0, C10:1, C10:2, C10:3, C10:4, etc.

For example, the lipid entity can be selected from the group consisting of α-linolenic acid, γ-linolenic acid, stearidonic acid, eicosapentaenoic acid, docosahexaenoic acid, linoleic acid, dihomo-γ-linolenic acid, arachidonic acid, docosatetraenoic acid, palmitoleic acid, vaccenic acid, paullinic acid, oleic acid, elaidic acid, gondoic acid, erucie acid, nervonic acid, mead acid, myristic acid, palmitic acid, stearic acid, 1,2-dipaimitoyl-sn-glycero-3-phosphoethanolamine (DPPE), GM11 ganglioside, GaM2 ganglioside, GM3 ganglioside, 1,2-dipalmitoyl-sn-glycero-3-phosphocholine (DPPC), 1,2-dioleoyl-sn-glycero-3-phospho-L-serine (DOPS), 1,2-dioleoyl-sn-glycero-3-phosphocholine (DOPC), a glycosphingolipid, a sphingolipid, phosphatidylinositol 4,5-bisphosphate (PIP2), a ceramide, cholesterol, ergosterol, phytosterol, a hopanoid, a steroid, fluorinated-GM1, fluorinated-GM2, fluorinated-GM3, 17-carboxy-1-oxo-heptadecyl, and an isoprenoid lipid (e.g., farnesyl (C-15) or geranylgeranyl (C-20)). In some embodiments, the lipid entity can be α-linolenic acid. In some embodiments, the lipid entity can be γ-linolenic acid. In some embodiments, the lipid entity can be palmitic acid. In some embodiments, the lipid entity can be vaccenic acid. In some embodiments, the lipid entity can be oleic acid. In some embodiments, the lipid entity can be elaidic acid. In some embodiments, the lipid entity can be myristic acid. In some embodiments, the lipid entity can be 17-carboxy-1-oxo-heptadecyl.

The attachment of a lipid entity to a peptide is referred to herein as lipidation. In some embodiments, the lipid entity is linked to the peptide covalently. In some embodiments, lipidation comprises the attachment of a peptide with any compound that is soluble in a cellular membrane (e.g., 10:1 in equilibrium constant $K_{assoc}\geq 10$).

In some embodiments, lipidation may comprise one or more of the following: attachment of diacylglycerol to the side chain of an N-terminal cysteine of a peptide via the sulfur atom; attachment of O-octanoyl to a serine or threonine of a peptide; and attachment of S-archaeol to a cysteine of a peptide. In some embodiments, lipidation may occur, for example, at any lysine, glutamic acid, aspartic acid, serine, threonine, cysteine, and/or tyrosine.

In some embodiments, lipidation may include fluorination. Fluorination can include the addition of one or more $C_6F_{13}$ chains. Without wishing to be bound by theory, it is thought that the presence of one or more $C_6F_{13}$ chains may allow a lipid entity to segregate from hydrocarbon lipid membrane components (see *J. Am. Chem. Soc.* 2007, 129, 9037-9043; *J. Phsy. Chem. B,* 2008, 112, 8250-8256; *J. Am. Chem. Soc.,* 2009, 131, 12091-12093).

In some embodiments, the lipid entity is attached to an amino acid residue which can be at or near the N-terminus of the peptide. In some embodiments, the lipid entity can be attached to an amino acid residue which is at or near the C-terminus of the peptide.

In some embodiments, the presence of at least one alkene in the structure of a lipid entity provides increased fluidity in a membrane (i.e., greater ability to move within the membrane) as compared to similar lipid entities lacking at least one alkene. In some embodiments, a lipid entity with greater fluidity is able to provide enhanced activity towards targets (e.g., receptors, ion channels, or enzymes) with a low density in a membrane. Without wishing to be bound by theory, it is possible that a lipid entity with increased ability to move within a membrane are able to encounter a low density target faster than a lipid entity with less mobility within a membrane.

The lipid entity can be linked to the peptide through a linker entity. As such, the composition can have the follow formula:

Lipid entity—Linker entity—Peptide

In some embodiments, the linker entity can have a length of between about 2 Å and 300 Å, inclusive. In some embodiments, the linker entity is between 30 Å and 150 Å, inclusive.

In some embodiments, the linker entity is attached to an amino acid residue which can be at or near the N-terminus of the peptide. In some embodiments, the linker entity can be attached to an amino acid residue which is at or near the C-terminus of the peptide.

In some embodiments, the linker entity can comprise one or more amino acids, which can either be natural or synthetic. For example, the linker entity can comprise a Glycine, Alanine, Leucine, Methionine, Phenylalanine, Tryptophan, Lysine, Glutamine, Glutamic Acid, Serine, Proline, Valine, Isoleucine, Cysteine, Tyrosine, Histidine, Arginine, Asparagine, Aspartic Acid, Threonine, or a combination thereof.

In some embodiments, the linker entity can comprise a peptide ("peptide linker"), e.g., between about 2 and 20 amino acid residues in length, or between about 5 and 10 amino acid residues in length. According to various embodiments, peptide linkers can be designed such that one or more α-helices are formed between the peptide described herein and a lipid entity. In some embodiments, a peptide linker may comprise a plurality of α-helices. In some embodiments, the plurality of α-helices is consecutive. In some embodiments, a plurality of α-helices is 2, 3, 4, 5, 6, 7, 8, 9, 10, 15, 20, or more α-helices.

In some embodiments, a peptide linker can comprise repeating units, for example a plurality of repeating glycine-asparagine (GN) units. In some embodiments, a peptide linker can comprise an epitope tag (e.g., a c-Myc tag) or other markers to allow for identification and/or characterization of provided agents and their fate in vitro and/or in vivo.

In some embodiments, the peptide linker can comprise the amino acid sequence of GGK or GG.

In some embodiments, the linker entity can comprise a non-peptide entity ("non-peptide linker"). In some embodiments, the linker entity can comprise ethylene glycol and/or aminoethylethanolamine (AEEA). In some embodiments, non-peptide linkers may be a synthetic polymer. According to various embodiments, the synthetic polymer may be any of a variety of lengths. In some embodiments, a linker entity comprising a synthetic polymer comprises a monomeric unit of the polymer. In some embodiments, a linker entity comprising a synthetic polymer comprises two or more monomeric units of a synthetic polymer (e.g., 2, 3, 4, 5, 6, 7, 9, 10, 20, 30, 40, 50, 100 or more monomeric units).

In some embodiments, a linker entity can comprise a polyethylene glycol (PEG). In Some embodiments, the average number of ethylene glycol units in the PEG is 2-20, e.g., 2, 3, 4, 5, 6, 7, 8, 9, 10, 11, 12, 13, 14, 15, 16, 17, 18, 19, or 20. In some embodiments, the linker entity can comprise PEG8, which means that the average number of ethylene glycol units is 8.

Non-limiting examples of suitable polymeric linkers include linkers with one or more monomeric units according to one of the following formulas:

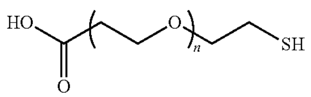

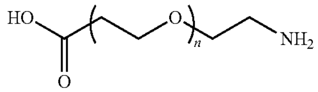

where n represents an integer greater than or equal to 1. In some embodiments, n is an integer between 2 and 50, 4 and 24, and/or 8 and 24, inclusive.

In some embodiments, the linker entity can have any one of the following structures:

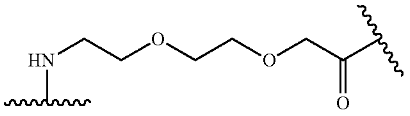

OEG

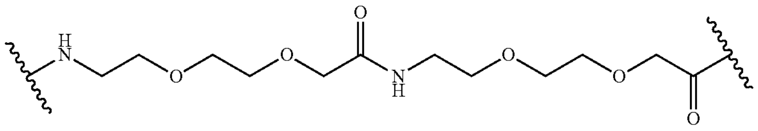

2xOEG

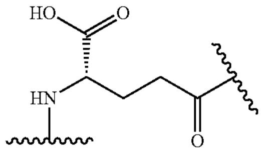

γGlu

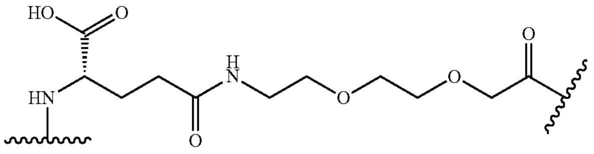

γGlu-OEG

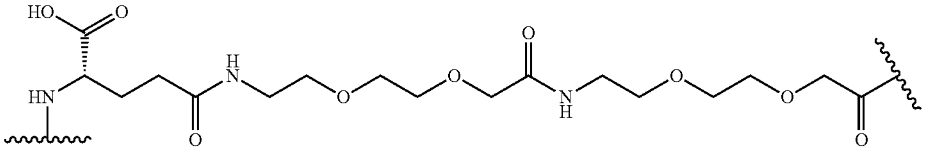

γGlu-2xOEG

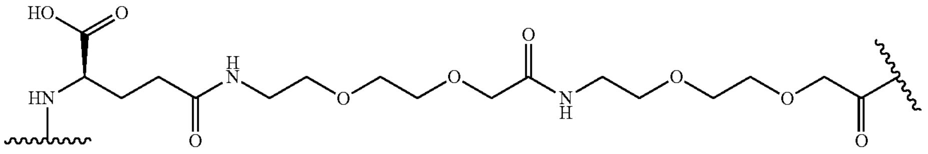

DγGlu-2xOEG

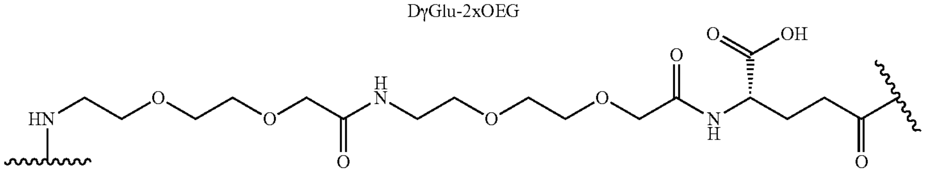

2xOEG-γGlu

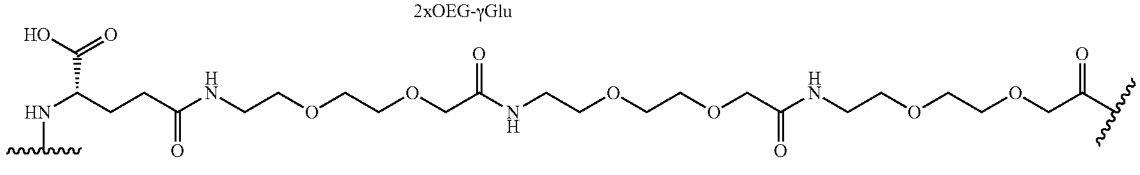

γGlu-3xOEG

-continued

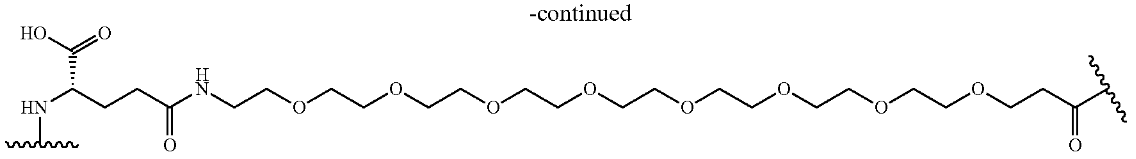

γGlu-8PEG

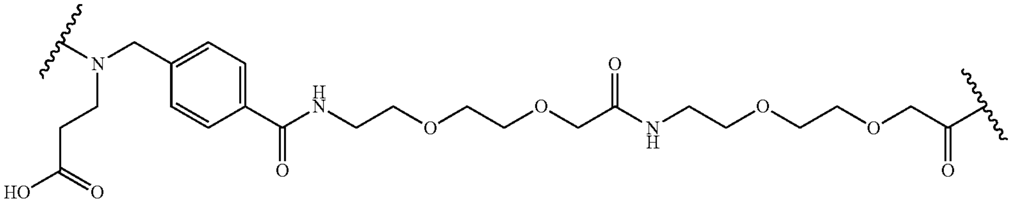

benzyl-βAla-2xOEG

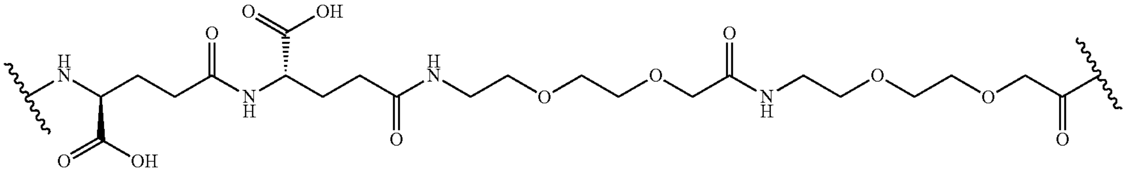

2xγGlu-2xOEG

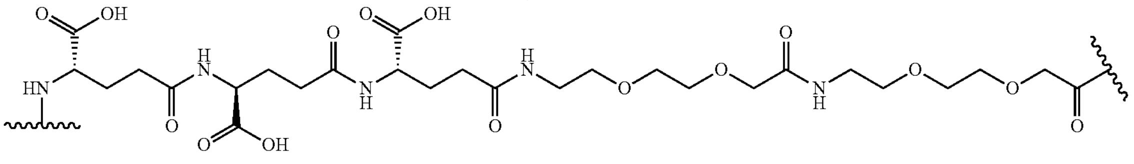

3xγGlu-2xOEG

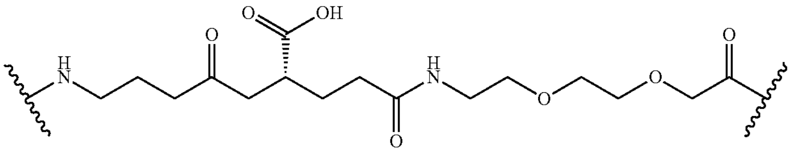

Abu-γGlu-OEG

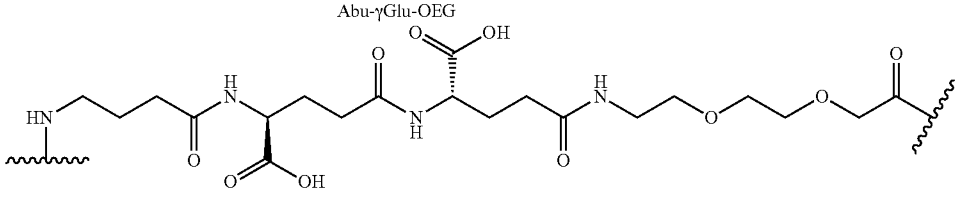

Abu-2xγGlu-OEG

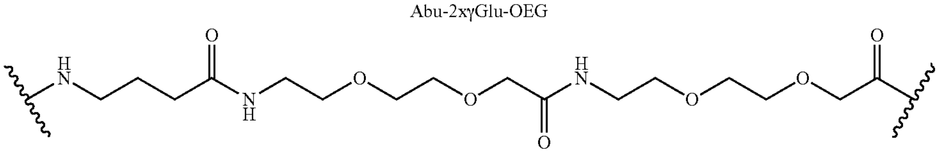

Abu-2xOEG

In some embodiments, a linker entity can comprise a monosaccharide, an oligosaccharide, or a polysaccharide, e.g., glucose, fructose, galactose, inulin, or a trisaccharide.

In some embodiments, a linker entity can comprise I-Ethyl-3-(3-Dimethylaminopropyl) carbodiimide (EDAC), Benzophenone-4-Isothiocyanate, Bis-((N-Iodoacetyl)Piperazinyl)Sulfonerhodarmine, Succinimidyl 2-(2-Pyridyldithio)Propionate (SPDP), 4-Azido-2,3,5,6-Tetrafluorobenzoic acid (ATFB), (N-((2-Pyridyldthio)ethyl)-4-Azidosalicylamide), Succinimidyl trans-4-(maleimidylmethyl)cyclohexane-1-car boxy late (SMCC), and/or N-(t-BOC)-aminooxyacetic acid. Those of skill in the art will be able to identify additional candidate linker entities according to known methods.

In some embodiments, a linker entity can comprise both a peptide and a non-peptide entity. For example, the linker entity can comprise both PEG8 and a peptide, e.g., a peptide having the amino acid sequence of GGK or GO.

In some embodiments, a linker entity is formed, at least in part, as a result of a click reaction, e.g., an azide-alkyne Huisgen cycloaddition reaction.

Additional examples of lipid entities, linker entities, and methods of lipidation can be found at US20160052982 and US20190022168, the contents of each of which are incorporated herein by reference.

Any embodiment of the lipid entities described herein and any embodiment of the linker entities described herein can be combined. For example, a combination of the lipid entity and the linker entity can comprise palmitic acid-γ-glutamic acid, palmitic acid-lysine, palmitic acid-γ-glutamic acid-lysine, myristic acid-lysine, 17-carboxy-1-oxo-heptadecyl-γ-glutamic acid-$(AEEA)_2$, AEEA-PEG, or 17-carboxy-1-oxo-heptadecyl-γ-glutamic acid-$(AEEA)_2$-lysine.

In some embodiments, the combination of the lipid entity and linker entity can be

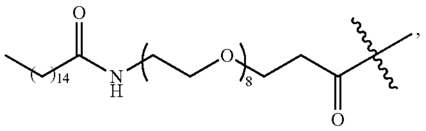

where the squiggly line denotes the point of coupling to the peptide.

In some embodiments, when lipidation occurs at the N-terminus of the peptide, palmitic acid, myristic acid, palmitic acid-γ-glutamic acid, palmitic acid-γ-glutamic acid-2xOEG, 17-carboxy-1-oxo-heptadecyl-γ-glutamic acid-$(AEEA)_2$, or cholesterol can be attached to the N-terminus of the peptide.

In some embodiments, when lipidation occurs at the C-terminus of the peptide, palmitic acid-lysine, palmitic acid-γ-glutamic acid-lysine, myristic acid-lysine, or 17-carboxy-1-oxo-heptadecyl-γ-glutamic acid-$(AEEA)_2$-lysine can be attached to the C-terminus of the peptide.

In some embodiments, the compositions described herein are soluble in water.

Administration of the Compositions

The therapeutically effective amount of a composition according to this disclosure can vary within wide limits and may be determined in a manner known in the art. For example, the composition can be dosed according to body weight. Such dosage will be adjusted to the individual requirements in each particular case including the specific composition being administered, the route of administration, the condition being treated, as well as the patient being treated. In another embodiment, the composition can be administered by fixed doses, e.g., dose not adjusted according to body weight. In general, in the case of oral or parenteral administration to adult humans, a daily dosage of from about 0.5 mg to about 1000 mg should be appropriate, although the upper limit may be exceeded when indicated. The dosage can be from about 5 mg to about 500 mg per day, e.g., about 5 mg to about 400 mg, about 5 mg to about 300 mg, about 5 mg to about 200 mg. The daily dosage can be administered as a single dose or in divided doses, or for parenteral administration it may be given as continuous infusion.

A therapeutically effective amount of a composition is that which provides an objectively identifiable improvement as noted by the clinician or other qualified observer.

The present disclosure also provides a pharmaceutical composition comprising the peptide composition described herein and a pharmaceutically acceptable carrier. The pharmaceutical compositions can be included in a container, pack, or dispenser together with instructions for administration. The compositions described herein can be administered topically, orally, nasally, transdermally, pulmonary, inhalationally, buccally, sublingually, intraperintoneally, subcutaneously, intramuscularly, intravenously, rectally, intrapleurally, intrathecally, or parenterally. In one embodiment, the composition is administered topically. For example, the composition is administered in the form of eye drops. In one embodiment, the composition is administered orally. In some embodiments, the composition is administered intravenously. In some embodiments, the composition is administered intrathecally. One skilled in the art will recognize the advantages of certain routes of administration.

The dosage regimen utilizing the compositions described herein is selected in accordance with a variety of factors including species, ethnicity, age, weight, sex and medical condition of the patient; the severity of the condition to be treated; the route of administration; the renal and hepatic function of the patient; and the particular composition employed. An ordinarily skilled physician or veterinarian can readily determine and prescribe the effective amount of the drug required to prevent, counter, or arrest the progress of the condition.

The compositions described herein can be administered once a day, twice a day, thrice a day, more than thrice a day, or once every few days.

Techniques for formulation and administration of the disclosed compositions of the disclosure can be found in *Remington: the Science and Practice of Pharmacy,* $19^{th}$ edition, Mack Publishing Co., Easton, Pa. (1995). In an embodiment, the lipidated peptides described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The lipidated peptides will be present in such pharmaceutical compositions in amounts sufficient to provide the desired dosage amount in the range described herein.

In some embodiments, the pharmaceutical composition can be formulated for topical administration. Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (wt/wt) active ingredient, although the concentration of active ingredient may be as high as the solubility limit of the active ingredient in the solvent. Formulations for topical administration may further comprise one or more of the additional ingredients.

In some embodiments, the pharmaceutical composition can be formulated for oral administration. Oral formulations containing the pharmaceutical composition described herein can be formulated into any conventionally used oral forms, including: tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, syrups, buccal forms, and oral liquids. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. In some embodiments are surface modifying agents which include nonionic and anionic surface modifying agents. For example, surface modifying agents include, but are not limited to, poloxamer 188, benzalkonium chloride, calcium stearate, cetostearyl alcohol, cetomacrogol emulsifying wax, sorbitan esters, colloidal silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

Methods of Treatment

The compositions described herein can be used to treat a variety of conditions including pain such as neuropathic pain, ocular pain, chronic pain, pain resulting from chemotherapy or radiation, pain resulting from nerve injury or nerve degeneration, and pain resulting from an inflammatory condition, dysesthesia, or allodynia. The compositions described herein can also be used to treat an inflammatory condition such as ocular inflammation, retinal inflammation, dry eye, uveitis, allergic conjunctivitis, and inflammation resulting from nerve injury or nerve degeneration.

In one aspect, the present disclosure provides a method of treating neuropathic pain with the compositions described herein. Neuropathic pain according to the present disclosure is a pain initiated or caused by a primary lesion or dysfunction in the nervous system. Neuropathic pain can be divided into “peripheral” (originating in the peripheral nervous system) and “central” (originating in the brain or spinal cord). For example, neuropathic pain syndromes include postherpetic neuralgia (caused by Herpes Zoster), root avulsions, painful traumatic mononeuropathy, painful polyneuropathy (particularly due to diabetes), central pain syndromes (potentially caused by virtually any lesion at any level of the nervous system), postsurgical pain syndromes (e.g., postmastectomy syndrome, postthoracotomy syndrome, or phantom pain), and complex regional pain syndrome (e.g., reflex sympathetic dystrophy or causalgia).

Neuropathic pain has typical symptoms like dysesthesias (spontaneous or evoked burning pain, often with a superimposed lancinating component), but the pain may also be deep and aching. Other sensations like hyperesthesia, hyperalgesia, allodynia (pain due to a normoxious stimulus), and hyperpathia (particularly unpleasant, exaggerated pain response) may also occur. The compositions of the present disclosure can be administered to ameliorate at least one of these symptoms.

Current therapy for neuropathic pain aims only at reducing symptoms, generally by suppressing neuronal activity. Thus, treatment options, e.g., non-steroidal anti-inflammatory drugs (NSAIDS), antidepressants, anticonvulsants, baclofen, neuromodulation modalities, or opiates, predominantly alleviate symptoms via nonspecific reduction of neuronal hyperexcitability rather than targeting the specific etiologies. The compositions of the present disclosure can be administered in combination with the current therapy for treating neuropathic pain. For example, the compositions of the present disclosure can be administered in combination with an NSAID, an antidepressant, an anticonvulsant, baclofen, a neuromodulation modality, or an opiate for treating neuropathic pain.

In another aspect, the present disclosure provides a method of treating ocular pain with the compositions described herein. Ocular pain can be co-incident with a number of conditions, including but not limited to trauma due to accidental or surgical injury, uveitis, dry eye, and diabetic neuropathy. The standard of care for treatment of ocular pain is typically either topically administered NSAJDs, or orally administered analgesic agents, such as NSATDS or opioids like hydrocodone. In some embodiments, the compositions of the present disclosure can be administered in combination with an NSAID or opioid for treating ocular pain.

In another aspect, the present disclosure provides a method of treating chronic pain with the compositions described herein. The compositions described herein can be used as non-opioid analgesics for treating chronic pain.

In another aspect, the present disclosure provides a method of treating pain resulting from chemotherapy or radiation. Commonly used chemotherapy drugs, such as vincristine sulfate, paclitaxel or cisplatin, may cause what is known as chemotherapy-induced peripheral neuropathy or paresthesia.

In another aspect, the present disclosure provides a method of treating pain resulting from nerve injury or nerve degeneration with the compositions described herein.

In another aspect, the present disclosure provides a method of treating pain resulting from an inflammatory condition, dysesthesia, or allodynia with the compositions described herein.

The compositions described herein can be administered in combination with an analgesic agent to treat pain. Examples of analgesic agents include, but are not limited to, paracetamol, an NSAID, a COX-2 inhibitor, an opioid, and medical *cannabis*.

In another aspect, the present disclosure provides a method of treating ocular inflammation or retinal inflammation with the compositions described herein. Ocular inflammation can be caused by a microbial infection of the eye. Such infection may be fungal, viral or bacterial. Current therapies for treating ocular inflammation include locally administered anti-cytokine or anti-inflammatory agents. In some embodiments, the compositions of the present disclosure can be administered in combination with an anti-cytokine or anti-inflammatory agent for treating ocular inflammation.

Anti-cytokine or anti-inflammatory agents include, but are not limited to, NF Kappa B inhibitors, for example corticosteroids, glucocorticoids such as flucinolonone; NSAIDs such as sulindac and tepoxalin; antioxidants such as dithiocarbamate; and other compounds such as sulfasalazine [2-hydroxy-5-[-4-[C2-pyridinylamino)sulfonyl]azo] benzoic acid], clonidine, and autologous blood-derived products such as Orthokine.

The compositions described herein can also be used to treat dry eye. Dry eye is primarily caused by the break-down of the pre-ocular tear film which results in dehydration of the exposed outer surface. Dry eye can be diagnosed through a comprehensive eye examination. Testing, with emphasis on the evaluation of the quantity and quality of tears produced by the eyes, may include: (a) patient history to determine the patient’s symptoms and to note any general health problems, medications or environmental factors that may be contributing to the dry eye problem; (b) external examination of the eye, including lid structure and blink dynamics; (c) evaluation of the eyelids and cornea using bright light and magnification; and (d) measurement of the quantity and quality of tears for any abnormalities. Special dyes may be put in the eyes to better observe tear flow and to highlight any changes to the outer surface of the eye caused by insufficient tears.

Without wishing to be bound by theory, there is a rationale that ocular inflammation as a result of pro-inflammatory cytokines and growth factors plays a major role in the underlying causes of dry eye. As such, locally administered anti-cytokine or anti-inflammatory agents are often used in the treatment of dry eye. In some embodiments, the compositions of the present disclosure can be administered in combination with an anti-cytokine or anti-inflammatory agent for treating dry eye.

In some embodiments, a therapeutically effective amount for treating ocular inflammation is an amount that reduces the extent of inflammation in the subject by at least 10%, at least 20%, at least 30%, at least 40%, at least 50%, at least 60%, at least 70%, at least 80%, at least 90%, or at least 95% compared to a placebo.

In some embodiments, a therapeutically effective amount for treating dry eye is an amount that increases the production of tears in the subject by at least 10%, at least 20%, at least 30%, at least 40%, at least 50%, at least 60%, at least 70%, at least 80%, at least 90%, at least 100%, or at least 150% compared to a placebo.

The compositions described herein can be used to treat uveitis such as noninfectious uveitis. Uveitis means inflammation in one or both of the patient's eyes. Uveitis is a wide range of inflammatory diseases of the eye, specifically the uvea. There are 3 basic layers of the eye the sclera and cornea on the outside, the retina on the inside, and the uvea in between. The uvea is comprised mostly of blood vessels and connective tissue, including pigmented cells. The different parts of the uvea are the iris in the front, the ciliary body in the middle, and the choroid located behind these, which lies around most of the eye. Sometimes uveitis can affect parts of the eye other than uvea, such as retina, vitreous, or optic nerve. Types of uveitis can be based on what part of the eye is affected. For example, anterior uveitis is the inflammation in the front of the eye, called iritis or iridocyclitis; intermediate uveitis is the inflammation in the middle part of the eye, or pars planitis or vitritis; posterior uveitis is the inflammation of the back of the eye, such as choroiditis, retinal vasculitis, retinitis, neuroretinitis, retinochoroiditis, or chorioretinitis.

Symptoms of uveitis commonly include redness, blurry vision, pain, light sensitivity, and floaters and flashes.

Noninfectious uveitis can result from an eye injury or a disease somewhere else in the patient's body. Typically, steroids or immunosuppressants are used to treat noninfectious uveitis. In some embodiments, the compositions described herein can be used in combination with a steroid or an immunosuppressant to treat noninfectious uveitis.

The compositions described herein can be used to treat allergic conjunctivitis. Allergic conjunctivitis is an eye inflammation caused by an allergic reaction to substances like pollen or mold spores. Typically, antihistamines, decongestants, or steroids are used to treat allergic conjunctivitis. In some embodiments, the compositions described herein can be used in combination with an antihistamine, a decongestant, or a steroid to treat allergic conjunctivitis.

The compositions described herein can be used to treat inflammation resulting from nerve injury or nerve degeneration.

The compositions described herein can be used to prevent any one of the diseases, disorders, or conditions described herein. For example, the compositions described herein can be used to prevent neuropathic pain, ocular pain, ocular inflammation, dry eye, uveitis, or allergic conjunctivitis.

With respect to combination therapies involving a first therapeutic agent (e.g., a composition of the present disclosure) and a second therapeutic agent (e.g., an anti-inflammatory agent, an opioid, an NSAITD, or an antidepressant), the first therapeutic agent can be administered concurrently with the second therapeutic agent; the first therapeutic agent can be administered before the second therapeutic agent; or the first therapeutic agent can be administered after the second therapeutic agent. The administrations of the first and second therapeutic agents can be separated by minutes or hours, e.g., one hour, two hours, three hours, four hours, five hours, or six hours.

Definitions

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein. It is to be understood that the terminology used herein is for the purpose of describing particular embodiments only, and is not intended to be limiting.

As used herein, the term "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "and/or," as used herein, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" may refer, in one embodiment, to A only (optionally including elements other than B); in another embodiment, to B only (optionally including elements other than A); in yet another embodiment, to both A and B (optionally including other elements); etc.

The terms "peptide," "polypeptide," and "protein" are used interchangeably herein and typically refer to a molecule comprising a chain of two or more amino acids (e.g., most typically L-amino acids, but also including, e.g., D-amino acids, modified amino acids, amino acid analogs, and amino acid mimetic). Peptides may be naturally occurring, synthetically produced, or recombinantly expressed. Peptides may also comprise additional groups modifying the amino acid chain, for example, functional groups added via post-translational modification. Examples of post-translation modifications include, but are not limited to, acetylation, alkylation (including methylation), biotinylation, glutamylation, glycylation, glycosylation, isoprenylation, lipoylation, phosphopantetheinylation, phosphorylation, selenation, and C-terminal amidation. The term peptide also includes peptides comprising modifications of the amino terminus and/or the carboxyl terminus. Modifications of the terminal amino group include, but are not limited to, desamino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). The term peptide also includes modifications, such as but not limited to those described above, of amino acids falling between the amino and carboxy termini. The term peptide can also include peptides modified to include one or more detectable labels.

The phrase "amino acid residue" as used herein refers to an amino acid that is incorporated into a peptide by an amide bond or an amide bond mimetic. The amino acid can either be natural or synthetic.

The terminal amino acid at one end of the peptide chain typically has a free amino group (i.e., the amino terminus). The terminal amino acid at the other end of the chain typically has a free carboxyl group (i.e., the carboxy terminus). Typically, the amino acids making up a peptide are numbered in order, starting at the amino terminus and increasing in the direction of the carboxy terminus of the peptide.

As used herein, the term "analog" refers to a variant or mutant polypeptide having one or more amino acid modifications compared to the wild type.

As used herein, the terms "treat," "treating," "treatment," and the like refer to reducing or ameliorating a disorder and/or a symptom associated therewith. It will be appreciated that, although not precluded, treating a disorder or condition does not require that the disorder or symptom associated therewith be completely eliminated. The terms "treat," "treating," or "treatment," do not include prevention.

As used herein, the term "prevent" refers to reducing or eliminating the onset of the symptoms or complications of a disease, condition, or disorder.

As used herein, a "subject" can be any mammal, e.g., a human, a non-human primate, mouse, rat, dog, cat, cow, horse, pig, sheep, goat, camel. In some embodiments, the subject is a human.

The term "pharmaceutical composition" refers to a mixture of the peptide composition disclosed herein with other chemical components, such as diluents or carriers. The pharmaceutical composition facilitates administration of the peptide composition to an organism such as a human. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Pharmaceutically acceptable carrier" means a carrier that is useful in preparing a pharmaceutical composition that is generally safe, non-toxic and neither biologically nor otherwise undesirable, and includes excipient that is acceptable for veterinary use as well as human pharmaceutical use. Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician.

As used herein, the singular forms "a," "an" and "the" include plural referents unless the context clearly dictates otherwise. Thus, for example, reference to "a solvent" includes a combination of two or more such solvents, reference to "a peptide" includes one or more peptides, or mixtures of peptides, reference to "a drug" includes one or more drugs, reference to "a device" includes one or more devices, and the like. Unless specifically stated or obvious from context, as used herein, the term "or" is understood to be inclusive and covers both "or" and "and".

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

Unless specifically stated or obvious from context, as used herein, the term "about" is understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

EXAMPLES

Example 1

Synthesis of Lipidated Peptides

All peptides were prepared using an Fmoc-tBu strategy. This utilizes an Fmoc protecting group on the N-terminus with side chain protecting groups being either tBu or Trt based depending on the specific functionality present. Activation utilized diisopropoylcarbodiimide in the presence of hydroxybenzotriazole (HOBT) to minimize racemization in DMF. Fmoc removal is facilitated with 20% piperidine in DMF at a ratio of 10 ml/g of resin. The peptide resin is washed with DMF and IpOH (10 ml of solvent/g of resin) following a deblocking step and following coupling steps. Upon completion of the linear peptide sequence, the peptide is cleaved from the solid support and simultaneously deprotected on the side chains using an acidolytic cleavage with TFA and cationic scavengers (water, triisoproplylsilane, 3,6-dioxa-1,8-octanedithiol (DODT), thioanisole, phenol) added according to presence of specific side chain protecting groups. Cleavage time is typically between 60 mnin and 120 min. The crude peptide is isolated by filtration to remove the spent resin beads and subsequently precipitated in ice cold methyl t-butyl ether. The precipitated peptide is collected using a sintered glass funnel and dried in drying oven until a constant weight is obtained.

The crude peptide is subsequently redissolved in an appropriate buffer system (eg. 20% AcOH in water) and purified by preparative reverse phase HPLC. Following purification, fractions which meet the minimum pool criterion of >95% are pooled and subsequently lyophilized. The final freeze-dried peptides are analyzed by analytical RP-HPLC, ESI-MS and other analytical methods such as Karl Fischer for water analysis, elemental analysis for Nitrogen for peptide content, and amino acid analysis.

Cell Culture Assays

PathHunter® β-Arrestin GPCR cell lines co-expressing the ProLink™ (PK) tagged GPCR (human Chemokine-like receptor 1, CMKLR1) and the Enzyme Acceptor (EA) tagged β-Arrestin were used. Activation of the GPCR-PK induces β-Arrestin-EA recruitment, forcing complementation of the two β-galactosidase enzyme fragments (EA and PK). The resulting functional enzyme hydrolyzes substrate to generate a chemiluminescent signal. The PathHunter® β-Arrestin assay monitors the activation of a GPCR in a homogenous, non-imaging assay format using a technology developed by DiscoverX called Enzyme Fragment Complementation (EFC) with β-galactosidase (β-Gal) as the functional reporter. The enzyme is split into two inactive complementary portions (EA for Enzyme Acceptor and PK for ProLink) expressed as fusion proteins in the cell. EA is fused to β-Arrestin and PK is fused to the GPCR of interest. When the GPCR is activated and β-Arrestin is recruited to the receptor, ED and EA complementation occurs, restoring β-Gal activity which is measured using chemiluminescent PathHunter® Detection Reagents.

Assay Design:

(a) Cell Handling: 1. PathHunter cell lines co-expressing the ProLink™ (PK) tagged GPCR (human Chemokine-like receptor 1, CMKLR1) and the Enzyme Acceptor (EA) tagged β-Arrestin were expanded from freezer stocks according to standard procedures. 2. Cells were seeded in a total volume of 20 μL, into white walled, 384-well microplates and incubated at 37° C. for the appropriate time prior to testing.

(b) Agonist Format: 1. For agonist determination, cells were incubated with peptide to induce response. 2. Intermediate dilution of peptide stocks was performed to generate 5× sample in assay buffer. 3.5 μL of 5× peptide was added to cells and incubated at 37° C. or room temperature for 90 to 180 minutes. Vehicle concentration was 1%.

(c) Signal Detection: 1. Assay signal was generated through a single addition of 12.5 or 15 μL (50% v/v) of PathHunter Detection reagent cocktail, followed by a one hour incubation at room temperature. 2. Microplates were read following signal generation with a PerkinElmer Envision™ instrument for chemiluminescent signal detection.

(d) Data Analysis: 1. Compound activity was analyzed using Chemical and Biological Information System (CBIS) data analysis suite (ChemInnovation, CA). 2. For agonist mod assays, percentage activity was calculated using the following formula: % Activity=100%×(mean RFU of test sample−mean RFU of vehicle control)/(mean MAX control ligand−mean RFU of vehicle control). RFU means relative fluorescence units.

TABLE 1

EC50 results for various peptides with N-terminal PEG8-Palmitic acid.

| Peptide Identifier | Chemerin analogs | EC50 nM |
|---|---|---|
| OK-101 | Gly-Gly-dTyr-Phe-Leu-Pro-dSer-Gln-Phe-dAla-Tic-Ser (SEQ ID NO: 10) | 2.6 |
| OK-102 | dAla-Gly-dTyr-Phe-Nle-Pro-dSer-Gln-Phe-dAla-Tic-dAla (SEQ ID NO: 7) | 2.3 |
| OK-103 | Ala-Ala-Tyr-Phe-Nle-Pro-Ser-Gln-Phe-Ala-Tic-dAla (SEQ ID NO: 11) | 43 |
| OK-104 | Ala-Ala-Phe-Tyr-Nle-Pro-Ser-Gln-Tyr-Ala-Tic-dAla (SEQ ID NO: 2) | 2.6 |
| OK-105 | Ala-Gly-Tyr-Phe-Nle-Pro-Thr-Asn-Phe-Ala-Tic-dAla (SEQ ID NO: 12) | 203 |
| OK-106 | Ala-Ala-Phe-Tyr-Nle-Pro-Thr-Gln-Phe-Ala-Tic-dAla (SEQ ID NO: 13) | 32.5 |
| Ok-107 | Ala-Ala-Tyr-Phe-Nle-Pro-Ser-Gln-Tyr-dAla-Phe-dAla (SEQ ID NO: 14) | 1708 |
| OK-108 | Ala-Gly-dTyr-Tyr-Nle-Pro-dSer-Gln-Phe-dAla-Phe-dAla (SEQ ID NO: 15) | 23.9 |

TABLE 1-continued

| EC50 results for various peptides with N-terminal PEG8-Palmitic acid. | | |
|---|---|---|
| Peptide Identifier | Chemerin analogs | EC50 nM |
| OK-109 | Ala-Gly-dTyr-Phe-Nle-Pro-dSer-Aad-Phe-Ala-Tic-dAla (SEQ ID NO: 3) | <.5 |
| OK-110 | dAla-Gly-dTyr-Tyr-Nle-Pro-dSer-Aad-Phe-dAla-Tic-dAla (SEQ ID NO: 6) | 11 |
| OK-111 | dAla-Gly-dTyr-Phe-Nle-Pro-dSer-Aad-Phe-dAla-Tic-dAla (SEQ ID NO: 17) | 15 |
| OK-112 | dAla-Gly-dTyr-Phe-Nle-Pro-dSer-Gln-fluorPhe-dAla-Tic-dAla (SEQ ID NO: 4) | 1.4 |
| OK-113 | NorV-Gly-dTyr-Phe-Nle-Pro-dSer-Gln-Phe-dAla-Tic-dAla (SEQ ID NO: 5) | <.5 |
| OK-114 | Ala-Gly-dTyr-Phe-Nle-Pro-dSer-Gln-Phe-Ala-Tic-dSer (SEQ ID NO: 6) | <.5 |
| OK-115 | Ala-Gly-Phe-Phe-Nle-Pro-Ser-Gln-Phe-Ala-Tic-dAla (SEQ ID NO: 18) | 12.4 |
| OK-116 | Gly-Gly-Phe-Phe-Nle-Pro-Ser-Gln-Phe-Ala-Tic-dSer (SEQ ID NO: 19) | 63.9 |

Example 2

Figure 1:
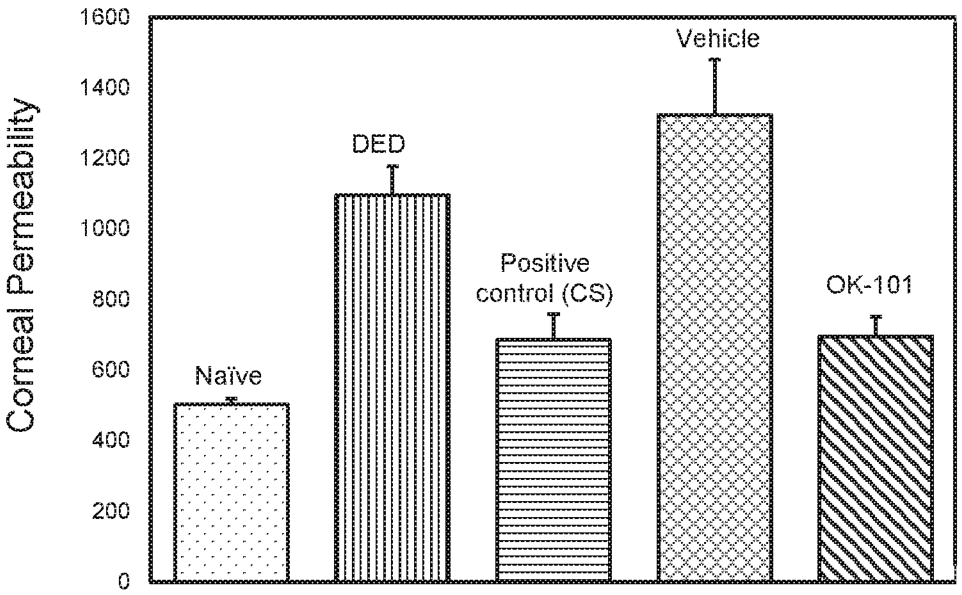
FIG. 1 is a graph showing that increase in corneal permeability due to dry eye was reduced significantly OK-101. Potency of OK-101 was comparable to cyclosporine (CS), an active ingredient of Restasis® (Allergan). The animal study was done with single dose. OK-101 has the following structure.

In FIGS. 1 and 2, assessment of corneal barrier function is performed as follows. Corneal staining was measured by penetration of Oregon Green Dextran (OGD). For baseline assessment, 0.5 μL of OGD was instilled on the cornea of both eyes, and the mice were housed in the dark for 1 minute before washing with balanced saline solution (BSS) and imaging. For corneal permeability assessment at Day 5, 0.5 μL of OGD was instilled on the cornea of both eyes, and the mice were immediately housed in the dark for one minute, followed by euthanization and immediate imaging. Eyes were washed with 2 mL of BSS. Digital images were captured, and the mean fluorescence intensity was measured with NIS Elements imaging software (Nikon).

In FIGS. 3 and 5, immunohistochemistry is used to detect CD4+ T cells. Enucleated mouse eyes with intact conjunctiva were suspended in optimal cutting temperature (OCT) compound and flash frozen in liquid nitrogen. Immunohistochemistry was performed on six micrometer frozen sections to detect and count the number of cells in conjunctival epithelium that stained positively for CD4, a biotinylated secondary antibody and NovaRED peroxidase. Positively stained cells were counted in the conjunctiva using Nikon imaging software.

In FIGS. 4 and 6, conjunctival goblet cells (GC) measurement is performed as follows. Enucleated mouse eyes with intact conjunctiva were fixed in 10% formalin and embedded in paraffin. Six-micrometer sections were stained with periodic acid-Schiff reagent. GC density in the superior and inferior conjunctiva was measured using Nikon imaging software.

What is claimed is:

1. A composition comprising a peptide selected from:

(SEQ ID NO: 2)
AAFY-Nle-PSQYA-Tic-dA;

(SEQ ID NO: 3)
AG-dY-F-Nle-P-dS-Aad-FA-Tic-dA;

(SEQ ID NO: 4)
dA-G-dY-F-Nle-P-dS-Q-fF-dA-Tic-dA;

(SEQ ID NO: 5)
NorV-G-dY-F-Nle-P-dS-QF-dA-Tic-dA;

(SEQ ID NO: 6)
AG-dY-F-Nle-P-dS-QFA-Tic-dS;

-continued and (SEQ ID NO: 7)
dA-G-dY-F-Nle-P-dS-QF-dA-Tic-dA, wherein Nle denotes norleucine, Tic denotes(S)-1,2,3,4-tetrahydroisoquinoline-3-carboxylic acid, dA denotes D-alanine, dY denotes D-tyrosine, dS denotes D-serine, Aad denotes α-aminoadipic acid, fF denotes fluorinated phenylalanine and NorV denotes norvaline; and wherein palmitic acid-PEG8 is linked at the N-terminus of the peptide, wherein PEG8 denotes an average number of 8 ethylene glycol units.

2. A pharmaceutical composition comprising the composition of claim 1 and a pharmaceutically acceptable carrier.

* * * * *